United States Patent [19]
Penny

[11] Patent Number: 4,922,758
[45] Date of Patent: May 8, 1990

[54] CELL ASSEMBLY FOR DETERMINING CONDUCTIVITY AND PERMEABILITY

[75] Inventor: Glenn S. Penny, Duncan, Okla.

[73] Assignee: Stim Lab, Inc., Duncan, Okla.

[21] Appl. No.: 233,158

[22] Filed: Aug. 17, 1988

Related U.S. Application Data

[62] Division of Ser. No. 52,458, May 20, 1987, Pat. No. 4,791,822.

[51] Int. Cl.$^5$ ........................................... G01N 15/08
[52] U.S. Cl. .................................................... 73/38
[58] Field of Search .................... 73/865.6, 866, 866.4, 73/38, 818, 40.5 R, 46, 47, 49.8; 166/280

[56] References Cited

U.S. PATENT DOCUMENTS

| | | | |
|---|---|---|---|
| 2,498,198 | 2/1950 | Beeson | 73/38 |
| 2,618,151 | 11/1952 | Leas | 73/38 |
| 2,705,418 | 4/1955 | Reichertz et al. | 73/38 |
| 2,762,294 | 9/1956 | Barnes et al. | 73/819 |
| 2,777,812 | 1/1957 | Powell et al. | 73/40.5 R |
| 3,708,560 | 1/1973 | Mayer et al. | 166/280 |
| 4,068,718 | 1/1978 | Cooke, Jr. et al. | 166/280 |
| 4,304,122 | 12/1981 | Tentor | 73/865.6 |
| 4,538,452 | 9/1985 | Hrvojic | 73/865.6 |
| 4,606,227 | 8/1986 | Walters | 73/865.6 |
| 4,643,019 | 2/1987 | Jones | 73/38 |
| 4,715,212 | 12/1987 | Johanson | 73/38 |

FOREIGN PATENT DOCUMENTS 277871  9/1927  United Kingdom .................... 73/47

Primary Examiner—Robert R. Raevis
Attorney, Agent, or Firm—Bill D. McCarthy

[57] ABSTRACT

A cell assembly for determining the conductivity and permeability of proppants in simulated subterranean formations comprising a plurality of vertically stacked cell units interconnected such that upon application of a compressive force the compressive force is transmitted equally throughout each of the cell units. Each of the cell units comprises a cell body member having a passageway extending therethrough; a lower piston connected to the cell body member such that one end thereof extends a selected distance into a lower portion of the passageway and an opposed second end extends outwardly therefrom for reciprocal movement within a cell body member of a second cell unit placed therebelow; and an upper piston member positionable in an upper portion of the passageway for reciprocal movement therein in response to force directed thereon, the upper piston member functioning as the lower piston member for a cell unit disposed thereabove. A plurality of shims are disposed within the passageway to define a proppant cavity therebetween. The upper and lower portions of each of the upper and lower piston members are provided with a groove about the peripheral edge portion adapted to receive a square ring such that a fluid tight seal is formed with the body member. A method and apparatus for conditioning a fracturing fluid to simulate downhole conditions are also disclosed.

4 Claims, 3 Drawing Sheets

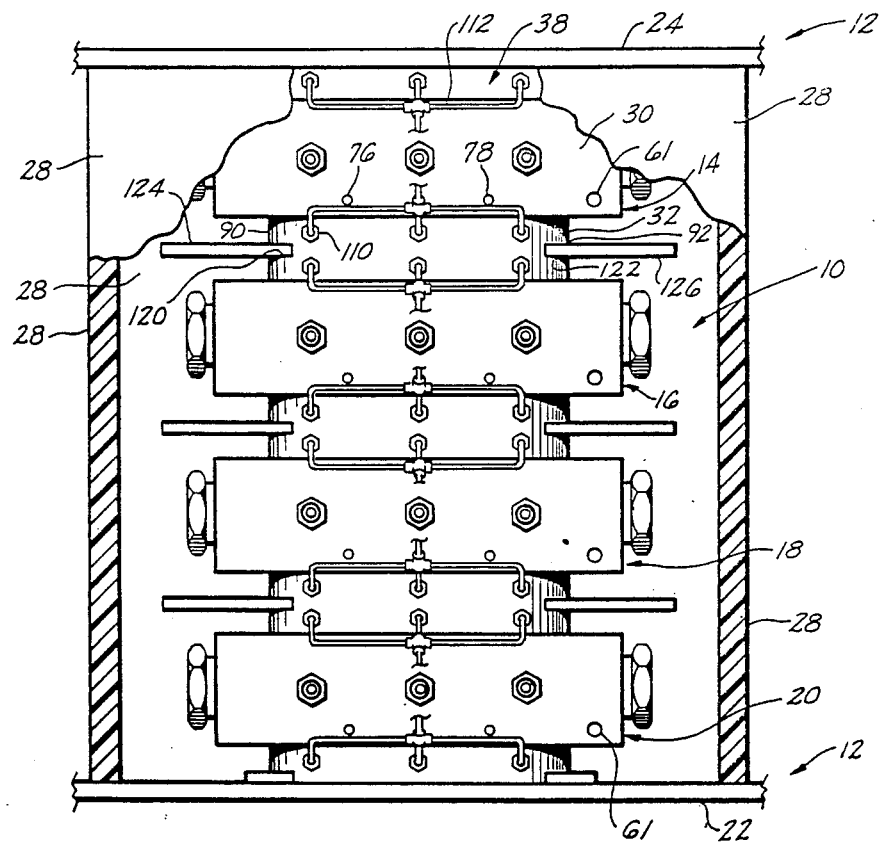
Fig. 1
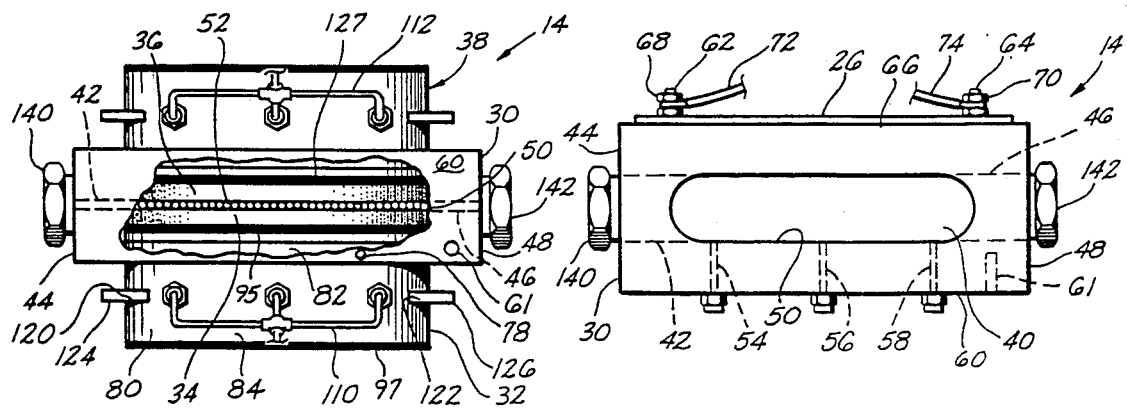
Fig. 2
Fig. 3

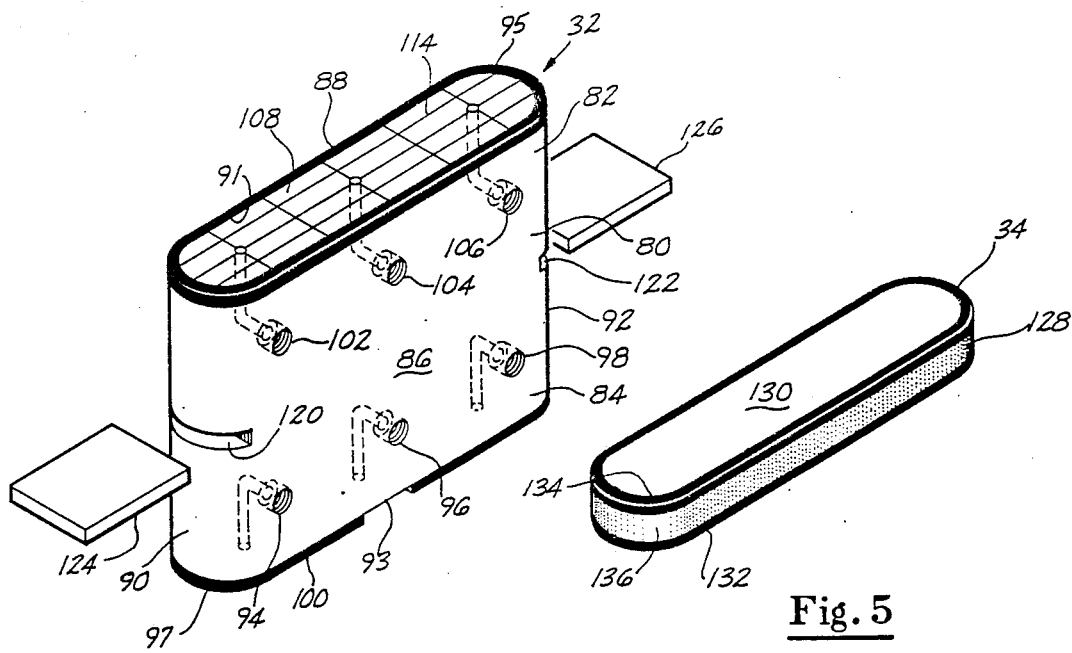
Fig. 4
Fig. 5
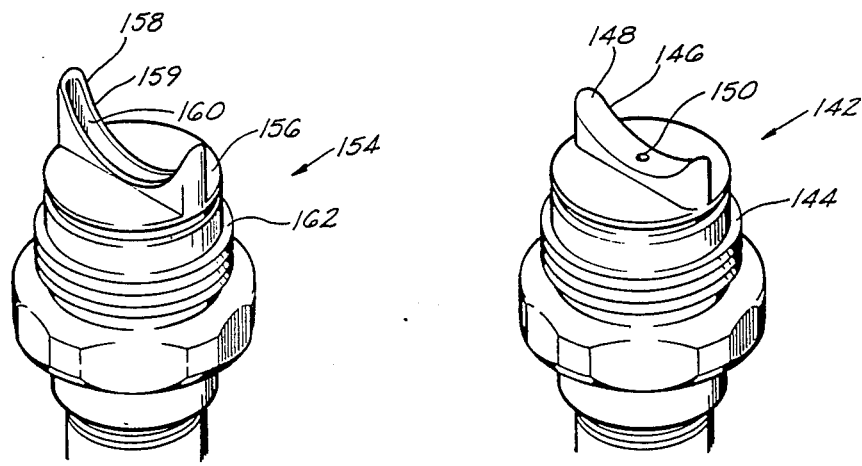
Fig. 6A
Fig. 6B

CELL ASSEMBLY FOR DETERMINING CONDUCTIVITY AND PERMEABILITY

This application is a division of application Ser. No. 052,458, filed May 20, 1987, now Pat. No. 4,791,822.

BACKGROUND OF THE INVENTION

1. Field of the Invention.

The present invention relates generally to a cell assembly for evaluating the conductivity and permeability of proppants, and more particularly but not by way of limitation, to a plurality of vertically stacked cell units for determining the effects of fracturing fluids on the conductivity and permeability of proppants at simulated subterranean conditions.

2. Brief Description of the Prior Art.

Knowledge of the characteristics of a subterranean formation is important for the efficient production of hydrocarbons from such a formation. In addition, knowledge as to the effect of fracturing fluids and additives on proppants injected into the formation is desirable so as to enhance hydrocarbon production. However, due to the complicated structure of many subterranean formations, and the interation of materials injected into the formation (such as fracturing fluids, additives, proppants and the like, as well as the interaction of fracturing fluids on the proppant within the formation) the characteristics of the proppant permeability often change.

Many methods have heretofore been proposed to determine the effect of fracturing fluids on the conductivity and permeability of proppants. However, such prior art procedures have generally failed to take into account the combined effects of the formation temperature, closure stress, formation structure (i.e. hardness), residence fluids and injected fracturing fluid as well as other factors prevalent in subterranean formations. Therefore, it would be highly desirable if a cell assembly could be develop which would enable one to simulate downhole conditions in fracturing treatments of subterranean formations, and especially if such cell assembly would be capable of simulating fluid leakoff and providing shear histroy modeling for fracturing fluid systems. It is to such a cell assembly and a method for determining the effect of conductivity and permeability of proppants that the subject invention is directed.

SUMMARY OF THE INVENTION

According to the present invention, an improved cell assembly is provided for determining the conductivity and permeability of proppants in simulated subterranean formations at the conditions encountered in such formations. Broadly, the cell assembly comprises a plurality of vertically stacked cell units interconnected for application of a compressive force (closure stress). The compressive force is transmitted equally throughout each of the cell units. Each of the cell units comprises a cell body member having a passageway extending therethrough; a lower piston connected to the cell body member such that one end thereof extends a selected distance into a lower portion of the passageway and an opposed second end extends outwardly therefrom for reciprocal movement within a cell body member of a second cell unit placed therebelow; and an upper piston member positionable in an upper portion of the passageway for reciprocal movement therein in response to force directed thereon, the upper piston member functioning as the lower piston member for a cell unit disposed thereabove. A plurality of shims are disposed within the passageway in a substantially parallel, spatial disposed relationship so as to define a proppant cavity therebetween. The shims, together with a square ring, form a fluid tight seal with the body member and are disposed substantially adjacent the upper and lower piston members so that fluid injected into the proppant pack cavity does not migrate around the edges of the shims.

An object of the present invention is to provide a method and apparatus for determining the effects of fracturing fluids on the conductivity and permeability of proppants.

Another object of the present invention, while achieving the before-stated object, is to provide a method and apparatus for determining the effects of gelled fracturing fluids on the conductivity and permeability of proppants in simulated downhole conditions.

Another object of the present invention, while achieving the before-stated object, is to provide a method and apparatus for efficiently and effectively determining the affect of gel fracturing fluids on the conductivity and permeability of propants under downhole temperature, pressure, fluid retention and formation structure.

Other objects, advantages and features of the present invention will become clear from the following detailed description when read in conjunction with the drawings and the appended claims.

BRIEF DESCRIPTION OF THE DRAWINGS

FIG. 1 is a schematic of a cell assembly constructed in accordance with the present invention wherein the cell assembly is positioned between plattens of a press.

FIG. 2 is a partially cutway, semi-detailed representation of a cell unit of the cell assembly of the present invention.

FIG. 3 is a top plan view of a cell body member of the cell unit of FIG. 2.

FIG. 4 is an isometric, partially cutaway view of a piston of the cell unit of FIG. 2 having a square ring disposed about the upper and lower ends of the piston.

FIG. 5 is an isometric view of a shim of the cell unit of FIG. 2.

FIG. 6A is an isometric view of an inlet conduit for dispersing a fracturing fluid into the cell body; and FIG. 6B is an isometric view of an alternate inlet conduit for the cell unit.

DETAILED DESCRIPTION

Figure 7:
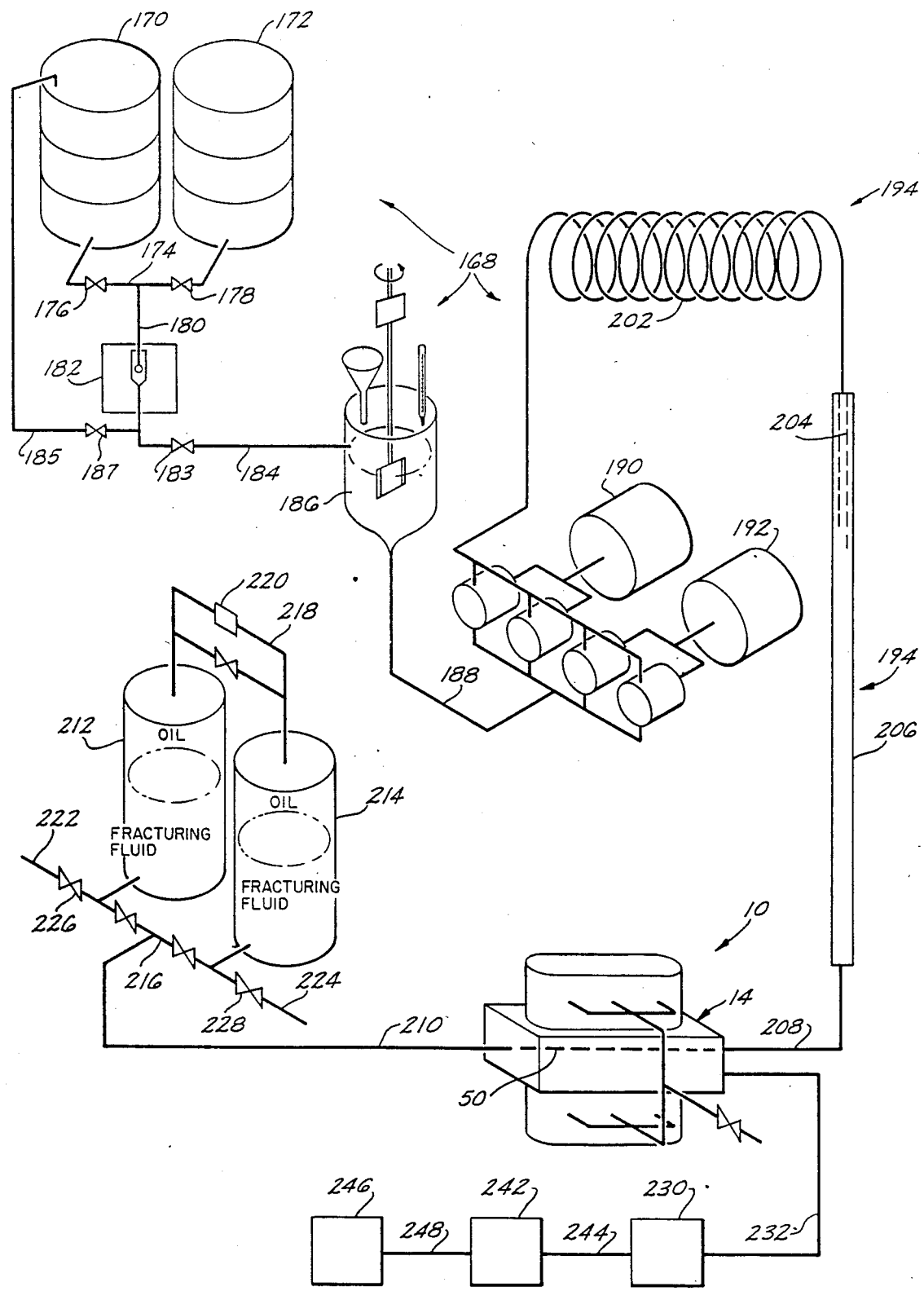
FIG. 7 is a schematic representation of an apparatus for conditioning fracturing fluid to simulate injection of the fracturing fluid into a subterranean formation.

Referring now to the drawings, and more specifically to FIG. 1, shown therein is a cell assembly 10 of the present invention and a hydraulic load frame or press 12. The cell assembly 10, which permits one to determine or evaluate the influence of typical fracturing fluid systems and additives on the conductivity and permeability of proppants under simulated downhole conditions in subterranean formations, comprises a plurality of vertically stacked cell units 14, 16, 18 and 20. The cell assembly 10 is supported in the vertical position on a lower platten 22 of the press 12; and an upper platten 24 of the press engages the uppermost cell unit 14 such that upon activation of the press 12 a predetermined hydraulic load is imparted to the cell assembly 10 by the plattens 22, 24. That is, the hydraulic load is imparted equally to each of the cell units 14, 16, 18 and 20 of the cell assembly 10.

The press 12 should have sufficient capacity to develop at least 15000 psi (103,500 kPa) closure stress on the cell assembly 10. To ensure uniform stress distribution, the plattens 22, 24 must be parallel. Further, the hydraulic pressuring source (not shown) for the press will desirably be capable of maintaining the closure stress (+ or −200 lbs. force or one percent, whichever is greater) over extended time periods. Further, the press 12 should be capable of loading rate changes of 5000 lbs. load per minute (500 psi/minute on a 10 square inch cell unit). Such presses or hydraulic load frames are commercial available units. For example, a Dake Mode 45-075 press, manufactured by the Dake Corporation, Grand Haven, Mich. 49417, or an equivalent press having a pressure controlling hydraulic pump can be used as the press 12. In lieu of the pressure controlling hydraulic pump a conventional hydraulic pump in combination with an air/oil booster system capable of the before-mentioned stress level and force control can be employed. Such equipment is also commerically available and well known in the art. Thus, no further description of the press 12 is believed necessary for one skilled in the art to have a clear understanding of the cell assembly 10 for determining the conductivity and permeability of proppants in accordance with the present invention.

To simulate the downhole conditions in the subterranean formation, the temperature of each of the cell units 14, 16, 18 and 20 must be controlled and maintained at a temperature substantially corresponding to the temperature of the subterranean formation. Such is accomplished by (a) controlling and regulating the temperature of the fluids injected into the cell units 14, 16, 18 and 20 by flowing the fluids through heated sand columns prior to introduction into the cell units; (b) setting the plattens 22, 24 of the press 12 to the predetermined test temperatures; (c) applying heat to each of the cell units 14, 16, 18 and 20 with thermocouple controlled heating strips, such as heating strip 26 (see FIG. 3); and (d) insulating the cell assembly 10 within the plattens 22, 24 of the press 12 with insulation 28. When untilizing the above procedures to regulate and control the temperature of the cell units 14, 16, 18 and 20, the test temperature can generally be maintained within about 3 degrees of the predetermined downhole temperature.

The cell units 14, 16, 18 and 20 of the cell assembly 10 may be employed to evaluate the influence of a specific fracturing fluid system on the conductivity and permeability of one proppant at simulated downhole conditions; to evaluate the influence of different fracturing fluid systems on the conductivity and permeability of a sepcific proppant; to evaluate the influence of several fracturing fluid systems on the conductivity and permeability on a plurality of proppants; or any combination of the above. That is, the cell units 14, 16, 18 and 20 may each be utilized to generate duplicate, accumulative data; or each of the cell units or combination thereof may be utilized to generate data reprsentative of different systems.

The cell units 14, 16, 18 and 20 of the cell assembly 10 are identical in construction, except as noted hereinbelow where certain components are shared by adjacent cell units. Thus, only cell unit 14 will be described in detail with reference to FIGS. 2 and 3. The cell unit 14 comprises a cell body member 30, a lower pistion 32, a pair of substantially parallel, spatially disposed shims 34, 36, and an upper piston 38. The shims 34 and 36 can be fabricated of quarried rock (as illustrated in FIG. 5); or the shims 34 and 36 can be fabricated of a metal wherein the shims have a thickness of from about 0.008 to 0.030 inches. However, when one desires to determine the rate of leakoff through the shims, the shims will be fabricated of quarried rock.

The cell body member 30, which is desirably fabricated of Monel-K-500, Hasteloy or stainless steel, is provided with a vertically disposed elongated passageway 40 extending therethrough, a fluid inlet port 42 formed in a first end 44 thereof, and an axially aligned fluid outlet port 46 formed in an opposed second end 48. As indicatead by the phantom lines in FIG. 2, the inlet port 42 and the outlet port 46 openingly communicate with the passageway 40 so that fluid communication is established therebetween. A central portion of the passageway 40, which is disposed between the shims 34, 36 and aligned with the inlet and outlet ports 42, 46, defines a proppant pack cavity 50 for receiving a proppant pack 52.

The cell body member 30 is further provided with a plurality of spatially disposed, substantially horizontally aligned ports 54, 56 and 58 extending through a side wall 60 of the cell body member 30. The ports 54, 56 and 58 intersect with the proppant pack cavity 50 so that the pressure drop ($\Delta P$) of a fluid driven through the proppant pack 52 can be monitored via the ports 54 and 58; and the internal pressure on the proppant pack can be monitored via the port 56.

As previously stated, to simuluate the downhole temperature of the subterranean formation in which the proppant pack 52 is being evaluated, the temperature of each cell unit is measured and controlled at a predetermined temperature; and the temperature of each cell unit is monitored at a thermocouple port in each cell unit, such as thermocouple port 61 in cell unit 14. As shown in FIG. 3, the cell body member 30 further comprises a pair of threaded studs 62, 64 extending from a side wall 66 thereof. The threaded studs 62, 64 are positioned through apertures (not shown) in the heating strip 26 so that the heating strip 26 can be secured adjacent the side wall 66 by bolts 68, 70 threadably connected to the threaded studs 62, 64, respectively. The heating strip 26 is connected to a power source (not shown) by electrical lead wires 72 and 74. Thus, upon activation of the thermocouple controlled heating strip 26, heat can be tansferred from the heating strip 26 to the proppant pack 52 in the proppant pack cavity 50 through the cell body member 30.

As illustrated in FIG. 1, the lower piston 32 of the cell unit 14 functions as the upper piston for the cell unit 16; the lower piston of the cell unit 16 functons as the upper piston for the cell unit 18; and the lower piston of the cell unit 18 functions as the upper piston for the cell unit 20. Thus, when a compressive force is exerted on the upper piston 38 of the cell unit 14 by the upper platten 24 of the press 12, the force is equally transferred through each of the cell units 14, 16, 18 and 20 because of the interconnection of the cell units via their respective upper and lower pistons. That is, the lower piston of each cell unit, such as the lower piston 32 of the cell unit 14, is disposed a selected distance into a lower portion of the passageway 40 and secured in a stable, stationary positoin by a plurality of set screws, such as set screws 76 and 78; and the upper piston, such as the upper piston 38 of the cell unit 14, is vertically movable through an upper portion of the passageway 40 in response to the compressive force applied thereto by the press 12.

The lower piston 32 and the upper piston 38 are of identical construction, and each is provided with a cross-sectional configuratoin corresponding to the cross-sectional configuration of the passageway of the cell units, such as the passageway 40 of the cell unit 14. Because each of the lower and upper pistons are identical in construction, and the lower piston 32 also functions as the upper piston for the cell unit 16, only the lower piston 32 will be described in detail hereinafter.

Referring more specifically to FIGS. 2 and 4, the lower piston 32 comprises an oval-shaped body member 80 having an upper portion 82 and an opposed lower portion 84. The oval-shaped body member 80 is further characterized as having a first side 86, an opposed second side 88, a first end portion 90 and an opposed second end portion 92. A recessed portion or groove 91 is formed about the upper portion 82 of the oval-shaped body member 80; and a recessed portion or groove 93 is formed about the lower portion 84 of the oval-shaped body member 80. The grooves 91 and 93 are sized to receive square rings 95 and 97 such that the square rings 95 and 97 extend outwardly and upwardly a predetermined distance from the oval-shaped body member 80. The configuration of the square rings 95 and 97, together with their disposition within the grooves 91, 93, respsectively, cooperate with the body member of the cell unit, such as the body member 30 of the cell unit 14, to form a fluid-tight seal therebetween.

The oval-shaped body member 80 is sized such that the upper portion 82, having the square ring 95 supported within the groove 91, is positionable within a lower portion of the passageway 40 of the cell body member 30 of the cell unit 14; and the lower portion 84 thereof, having the square ring 97 supported within the groove 93, extends outwardly from the cell body member 30 of the cell unit 14. The lower portion 84 of the cell body member 30 is then positionable within an upper portion of the passageway of the cell body of the cell unit 16 disposed below and in an aligned, spatial relationship with the cell unit 14. As previously stated, the upper portion of the oval-shaped body member 80 is secured in a stable, stationary position within the lower portion of the passageway 40 of the cell unit 14 by the set screws 76, 78; and the lower portion of the oval-shaped body member 80 is positioned in the upper portion of the passageway of the cell unit 16 so as to be vertically movable therein in response to force exerted on the upper piston 38 of the cell unit 14 by the press 12. That is, the upper portion of the upper piston 38 of the cell assembly 10 operably engages the upper platten 24 of the press 12; and the lower end portion of the lower piston of the cell unit 20 is supported on the lower platten 22 of the press 12. Thus, as a force is developed by the press 12, the force is transmitted through each of the cells 14, 16, 18 and 20 by their respective upper and lower pistons.

A first set of ports 94, 96 and 98 are disposed in the oval-shaped body member 80 so as to extend through the first side 86 thereof and a lower side 100; and a second set of ports 102, 104 and 106 are disposed in the oval-shaped body member 80 so as to extend through the first side 86 thereof and an upper side 108. The first set of ports 94, 96, 98 are connected to a volumetric measuring device (not shown) via a manifold assembly 110 (see FIGS. 1 and 2) so that the rate of leakoff of fluid through the lower shim 34 of the cell unit 14 can be determined as fluid is passed through the proppant pack cavity 50 of the cell body 30. Similarly, the second set of ports 102, 104 and 106 are connected to a volumetric measuring device (also not shown) via a manifold assembly 112 so that the rate of leakoff of fluid through the shim 36 of the cell unit 14 can be determined as fluid is passed through the proppant pack cavity 50 of the cell body member 30.

To assist in the delivery of the fluid to the first set of ports 94, 96 and 98, a plurality of grooves 114 are formed in the upper side 108 of the body member 80, the grooves 114 intersecting the ports 94, 96 and 98 substantially as shown. Similarly, a plurality of grooves (not shown, but substantially identical in design and function to the grooves 114) are formed in the lower side 100 of the oval-shaped body member 80.

The body member of each of the piston members is further characterized as having a substantially centrally disposed slot formed in each end thereof, such as slots 120, 122 formed in the first and second end portions 90, 92 of the oval-shaped body member 80. The slots 120, 122 are designed to receive slat members 124, 126 respectively, for assisting in the leveling of the cell assembly 10, as well as to provide a means to determine the height (or width as sometimes called) of the proppant pack 52. In addition, the slat members 124 and 126 cooperate to stabilized the shims 34, 36 in the desired spatial relationship when permeability and conductivity properties of the shims 34, 36 are being evaluated by passage of a fluid through the proppant pack cavity 50 of cell body member 30 in the absence of the proppant pack 52. The use of the slat members 124, 126, in combination with each of the cell units, will be further described hereinafter with reference to the operations of the cell assembly 10.

Referring now to FIG. 2, the shims 34, 36 are disposed within the passageway 40 of the cell body member 30 in a substantially parallel, spatial relationship so as to define the proppant pack cavity 50 therebetween. The shims 34 and 36 are substantially identical in construction and cooperate with the square rings 95, 97 and the cell body member 30 to form a fluid tight seal therebetween so that fluid passing through the proppant pack cavity 50 formed in the cell body member 30 is prevented from migrating or flowing around the shims 34 and 36. Fluid migration is further prevented by the application of a high temperature silicone sealant around the periphery of each of the shims 34, 36 to form a gasket as will be described hereinafter. Thus, the shims 34 and 36 are provided with an oval-shaped peripheral configuration substantially corresponding in size to the cross-sectional configuration of the passageway 40. The shim 34 abuts the square ring 95 disposed about the upper portion of the lower piston 32, and the shim 36 abuts a square ring 97 disposed about the lower end of the upper piston 38. Thus, force imparted to the upper piston 38 by the press 12 is transmitted to the shims 34 and 36, and thus the proppant pack 52 disposed within the proppant pack cavity 50.

In order to simulate the subterranean formation the shims 34 and 36 can be formed of quarried rock substantially corresponding to the structure of the formation being evaluated. Further, since it is desirable to determine the effects of a fracturing fluid, proppant and the like on the formation, the shims 34, 36 are substantially uniform in thickness.

Referring now in FIG. 5, the shim 34 fabricated of quarried rock is illustrated. The shim 34 and the shim 36 are substantially identical in structure and function. Thus, only shim 34 will be described in detail hereinafter. The shim 34 is characterized as comprising an oval-shaped body member 128 having a substantially upper planar surface 130, a substantially parallel, lower planar surface 132, and a peripheral edge portion 134. The oval-shaped body portion is sized so as to be positionable within the passageway 42 of the cell body member 30 and to abut the square rings disposed about the adjacent end portion of one of the pistons. Thus, when a compressive force is applied to the cell units, the shims compress the square rings against the side walls of the cell body members so that a fluid-tight seal is formed therebetween.

To further assist in the formation of a fluid-tight seal within the passageway of each of the cell units, a resilient gasket 136 is disposed around the peripheral edge portion of each of the shims, such as the edge portion 134 of the shim 34. The gasket material should be formed of an elastomeric material which is inert to the test solution, will withstand the temperature and pressures to which the cell unit 14 is subjected, and will adhere to the structure of the shim 34. Desirable results have been obtained when the material employlod to form the gasket 136 around the peripheral edge portion 134 of the oval-shaped body portion 128 is RTV auto gasket sealer manufactured and distributed by G.E. Corporation.

As shown in FIG. 2, the proppant pack 52 is positioned within the proppant pack cavity 50 defined by the shims 34, 36. The proppant pack 52 can be disposed in the proppant pack cavity 50 by placement on the loer shim 34 during the assembly of the cell units, such as the cell unit 14; or the proppant can be injected into the proppant pack cavity 50 via the fluid inlet port 42 in a sufficient quantity to form the proppant pack 52. However, in either instance, a sufficient amount of proppant is employed to fill the proppant pack cavity 50 and thus form the proppant pack 52 disposed therein. The amount of proppant utilized in the formation of the proppant pack 52 is an amount effective to provide from about 0.5 to about 4 pounds of proppant per square foot of the proppant pack cavity. The amount of proppant forming the proppant pack 52 can vary, but will generally be at an amount effective to provide from about 0.5 to about 4 lbs. of proppant per square foot of the proppant pack cavity 50, and more desirably about 2.0 lbs of proppant per square foot of the proppant pack cavity 50. The chemical makeup of the proppants used to form the proppant pack 52 are well known in the art and the particular proppant chosen will be determined by the nature of the test conducted, as well as the properties to be determined on the proppant.

When placing the proppant into the proppant cavity 50 during assembly of the cell unit, such as the cell unit 14, the lower piston 32 and the shim 34 are positioned within the passageway 40. Thereafter, the proppant is placed on the shim 34, and leveled to insure a substantially uniform pack width of the proppant on the shim 34. Thereafter, the shim 36 is positioned in place as is the upper piston 38. When placing the proppant on the shim 34 care should be exercised to insure that the proppant is not subjected to vibration or tamping as such will concentrate fines of the proppant in the lower portion of the proppant pack 52.

Because of the unique design of each of the cell units 14, 16, 18 and 20 of the cell assembly 10, the proppant can be injected into the proppant pack cavity 50 to provide the proppant pack 52. This permits one to obtain data on the structural properties and characteristics of the shims 34, 36 in either the presence of the proppant pack 52 or the absence thereof. In other words, a larger variety of data can be obtained using the cell assembly 10 of the present invention than has heretofore been achievable using prior art cells and test methods.

The cell unit 14 further comprises an inlet conduit 140 and an outlet conduit 142. When introducing a fluid, such as a saline solution, into the proppant pack cavity 50 of the cell unit 14 via the inlet conduit 140, the inlet conduit 140 and the outlet conduit 142 are substantially identical in construction. Thus, only the outlet conduit 142 will be described with reference to FIG. 6B. The outlet conduit 142 is provided with a threaded end portion 144 and a collector member 146 centrally supported thereon so as to extend therefrom substantially as shown. The collector member 146 is provided with a distal end 148 having an arcuate shaped surface substantially corresponding to the configuration of the second end 48 of the cell body member 30 defining the proppant pack cavity 50. A bore hole 150 extends through the collector member 146 for establishing fluid flow through the outlet conduit 142. The outlet conduit 142 is threadably connected to the outlet port 46 of the cell body member 30 such that a fluid-tight seal is formed therebetween.

Referring now to FIG. 6A, a second embodiment of an inlet conduit 154 is illustrated. The inlet conduit 154 is provided with an end portion 156 having a hollow injection member 158 supported thereon substantially as shown. The hollow injection member 158 is provided with an arcuate shaped distal end 159 such that when the inlet conduit 154 is positioned within the fluid inlet port 42 of the cell body member 30, the hollow injection member 158 is disposed substantially flush with the cell body member 30 defining the adjacent end portion of the proppant pack cavity 50. The hollow injection member 158 is further provided with a distribution channel 160 formed therethrough, the distribution channel 160 being shaped to provide a constant area transition from pipe to slot and thus substantially disperse fracturing fluid across the proppant pack cavity 50 which represents a simulated fracture cavity. By providing the injection member 158 with the distribution channel 160 as described, the shear profile from pipe to slot is essentially equivalent.

The end portion 156 of the inlet conduit 154 is provided with externally disposed threads 162 adapted to matingly engage internally disposed threads (not shown) of the inlet port 42. Thus, the inlet conduit 154 can be connected to the cell body member 30 via the inlet port 42 thereof to provide a fluid-tight seal therebetween.

The cell assembly 10 described above, and comprising the cell units 14, 16, 18 and 20, provides an efficient and effective means for simulating the downhole conditions of a subterranean formation, while at the same time permitting one to utilize the cells to determine the effect of fracturing fluids on proppants, subterranean formations, and the like. Thus, the cell assembly 10 overcomes many of the problems heretofore inherent in cell designs and cell assemblies for simulating downhole conditions.

In order to simulate the downhole conditions of a subterranean formation, and the effect of fracturing fluids on such formations, it would be desirable if one could develop a system for conditioning the fracturing fluids prior to injection into the cell units, such as the cell unit 14, of the cell assembly 10. The fracturing fluid can be prepared and conditioned to simulate the downhole conditions using an apparatus 168 schematically illustrated in FIG. 7. A pair of vessels 170, 172 (which function as fracturing fluid reservoirs) are manifolded together by a conduit 174. Valves 176, 178 are disposed within the conduit 174 so that the fracturing fluid can be selectively removed from one of the vessels 170, 172. A conduit 180 is connected to the conduit 174 at a position between the valves 176, 178 so that fulid communication is established between the conduits 174 and 180. The conduit 180 is connected to an inlet port (not shown) of a progressive cavity or screw pump 182, and a conduit 184 is connected to an outlet port (also not shown) of the pump 182 such that fluid passing therethrough can be fed via the conduit 184 to a blender 186. A valve 183 is disposed within the conduit 184; and a conduit 185 is connected to the conduit 184 and the vessel 170 upstream of the valve 183. A valve 187 is disposed within the conduit 185. Thus, when the valve 183 is closed and the valve 187 is opened, the fluid passing from the vessels 170, 172 through the pump 182 is recirculated to the mixing vessel 170 to aid in the mixing of the constituents forming the base gel.

Thus, the base gel to be tested in the system is batch mixed by adding gel and additives to the vessels 170, 172 while circulating the resulting composition with the pump 182 via the conduit 185 at a rate of about 20 gallons per minute. Once the base gel is determined to be substantially uniform, the valve 187 is closed and the valve 183 is opened. The base gel, containing the additives, is then fed through the blender 186 by the pump 182 and the conduit 184 where the fluid is stirred and delayed complexor and sand, if desired in the makeup of the fracturing fluid, are added. The fluid is removed from the blender 186 via a conduit 188 for passage through intensifier pumps 190, 192 which pressurize the fluid to 1000 psi for delivery at a rate of about ½ per minute. The particular pressure and flow rate of the fluid from the intensifier pumps 190, 192 is predetermined to simulate the downhole conditions in the formation after passage of the fluid through the tubing and fracturing simulator 194 prior to entry into the cell units of the cell assembly 10, such as the cell unit 14.

The tubing and fracturing simulator 194 comprises a predetermined length of a first tubing 202, a predetermined length of a second tubing 204, and a heat exchanger 206 disposed about the tubing 204 for heating the fluid passing therethrough. The first tubing 202 is provided with a internal diameter less than the internal diameter of the second tubing 204 so that the shear rate on fluid passing through the first tubing 202 simulates pumping the fluid through downhole tubing (1000–1500 reciprocal seconds), while the second tubing 204 is sized to represent downhole conditions in the formation, both as to shear rate and temperature. That is, the fluid is subjected to shear at a rate of 40 to 50 reciprocal seconds while undergoing heat up to formation temperatures, and such temperatures and shear rates are selected to represent the average cool down temperature and conditions at a point within 50 feet of the wellbore in formations at a depth of from about 5000 to about 10000 feet.

The residence time in the tubing and fracturing simulator 194 is approximately 5 to 10 minutes so that the fluid becomes fully complexed. That is, when the fluid is fed to the tubing and fracturing simulator 194 at 1000 psi and a rate of about ½ to 1.0 gallons per minute, the length of the first tubing 202 (i.e. a quarter inch or three-eigths inch tubing) is from about 250 feet to 1000 feet and the length of the second tubing 204 (i.e. a one inch tubing) is from about 50 feet to 200 feet. Thus, the fluid is retained in the tubing and fracturing simulator 194 for about 10 minutes and the shear rate on the fluid is reduced from about 1000 reciprocal seconds to about 40–50 reciprocal seconds while undergoing heat up to the formation temperatures of from about 160° C. to about 200° F.

The fluid is directed from the second tubing 204 of the tubing and fracturing simulator 194 via a conduit 208 into the cell units of the test cell assembly 10, such as the cell unit 14. The fluid flowing through the cell unit 14 is at the desired shear rate of from about 40–50 reciprocal seconds and the flow of the fluid is through the proppant pack cavity 50 of the cell unit 14.

The fluid exits the cell unit 14 via a conduit 210 for delivery to high pressure knock-out vessels 212, 214 where the sand-laden fluid can be collected and dumped, while maintaining a constant pressure of about 1000 psi on the system. The knock-out vessels 212, 214 are manifolded together via conduits 216 and 218, and a piston 220 is disposed within the conduit 218 for effective separation of the desired constituents from the fluid. Drain lines 222, 224 are connected to the conduit 216 and 218 so that fluid communication can be established therebetween. Valves 226, 228 are disposed within the drain lines 222, 224, respectively, for selective removal of fluid from the knock-out vessels 212 and 214.

Data obtained from the measurement of the fluid passing through the cell unit 14 of the cell assembly 10 is fed to a processing computer 230, such as a Validyne DA-380, via a plurality of input lines, such input lines being represented diagrammatically by line 232. Thus, line 232 represents the input lines for data generated by measurement of the closure pressure, pressure drop, flow rate, width of the proppant pack and temperature for each cell unit. The data generated in the processing computer 230 is then fed to a second computer 242 via input line 244. For tabulation of the data, the data is transmitted to a printer 246 via input line 248. The second computer 242 can be any suitable computer, such as an IBM-PC or Epson computer, and the printer 246 can be any suitable printer compatible with the second computer 242.

To assist one in fully understanding the data generated with the cell assembly 10, as well as the set up of the cell assembly 10 for various measurements, the following procedures are set forth.

EQUIPMENT AND PROCEDURES-CASE I

Cell Units

The cells used in this study each had a 10 squared inch flow path. Four cell units, i.e. cell units 14, 16, 18 and 20, were stacked so that the walls of the simulated fracture were formed by the upper and lower pistons, such as lower piston 32 and the upper piston 38 of cell unit 14. As previously stated, the lower piston 32 of the cell unit 14 functions as the upper piston for the cell unit 16. The bottom pistons of each cell unit were leveled and set with the set screws, such as set screws 76 and 78 so that the lower piston 32 was set to within 0.001 inch from side-to-side and end-to-end. The cell assembly is illustrated in FIG. 1.

Leveling

Proppant samples were leveled on the lower piston of each cell unit, such as the lower piston 32 of the cell unit 14. A concentration of about 2 lbs. per square inch of proppant was utilized. As each cell unit was stacked the pack width from side-to-side and end-to-end were set within 0.001 inch before positioning the other cells.

The Hydraulic Load

The hydraulic load was supplied by a Dake Model 45-086 hydraulic press modified with an air-to-oil intensifier system. The load was recorded by a temperature compensated electronic cell. Load was applied at a rate of 100 psi per minute.

The Drive Fluid System

The drive fluid system for introducing the test fluid into the cell units consisted of a series of nitrogen driven TEFLON lined accumulators i.e. polytetrafluoroethlene-lined accumulators. The test fluids were deoxygenated by bubbling nitrogen through the cell. The nitrogen was deoxygenated by passing it through a tube of copper turnings at 750° F. The oxygen content of each accumulator was checked chemically prior to running to insure an oxygen content of less than 20 ppb. All fluid contact points in the flow system were protected from iron. The inlet ports of the cells and pressure sensing outlet ports contained replaceable Hasteloy filters and/or screens. The fluid was filtered prior to introduction into the cell units and prior to flowing through the back pressure and flow rate equipment with monel, 7 micron in-line filters. The system pressure was set at 400 psi.

The Flow Rate

The flow rate was recorded electronically by measuring the pressure drop of the filtered fluid through a 20 micron Hasteloy disc. The pressure drop was measured with Validyne DP-15 transducers which were spanned to read the measured rate.

Differential Pressure

The differential presure through each cell unit was measured with a Validyne DP-15 transducer. Each transducer was isolated and zeroed hourly, and the span was checked daily with a column of water. The trasnsducer signals were conditioned with a Validyne DA-380 programmable monitoring station to within 0.0001 psi accuracy.

Width

The width of the proppant pack at each end was determined at 1000 psi with telescoping gauges and micrometers. The average values were set with Phillips LVDT postioin sensors, which then monitored the width electronically. To assist in such measurements, the slat members 124 were inserted within the slot 120 of each of the upper and lower pistons, such as lower piston 32 and upper piston 38 of the cell unit 14, and the distance between the slat members monitored to determine the width of the proppant pack as pressure was applied thereto.

Temperature

The temperature of the cells and fluid flowing therethrough was regulated by (1) first flowing the fluid through a heated sand column; (2) setting the press plattens to the test temperature; (3) applying heat to each cell with thermocouple controlled heating strips; and (4) insulating the entire assembly. The test temperature was maintained within 3 degrees of the desired temperature.

Data Outputs

Data outputs of closure pressure, pressure drop, flow rate, width, and temperature for each cell unit were fed through a Validyne DA-380 processing computer. The temperature was used to calculate the viscosity of the flowing fluid from curve fitting programs. Scaled inputs were used to calculate conductivity and permeability. All outputs and calculations from the processing computer were recorded with a second computer, an IBM-PC, and Epson printer.

Silica Saturation

Silica saturation was achieved by flowing the deoxygenated fluid through a heated 350 ml monel column filled with 100 mesh sand. The column was heated with a mantle to 25° F. in excess of the test temperature so that the fluid would dissolve all the silica required prior to reaching the proppant positioned within each cell unit.

Core Preparation

Ohio Sandstone quarry blocks were cut into ⅜ inch slabs 1½ inches wide and 7 inches long. The corners were rounded to fit the configuration of the passageway in each of the cell body members of the cell units. The cores were sealed in place within the cell body member utilizing a high temperature silicone sealant.

PROCEDURE FOR CONDUCTIVITY AND LIQUID PERMEABILITY MEASUREMENTS

1. The cells were loaded with about 2 lbs. per square foot of the proppant sample to be tested and the proppant was leveled.

2. The cells were stacked to within 0.005 inch from top to bottom and were positioned between the plattens of the Dake Press. Pressure was increased to 500 psi and the system was evacuated and saturated with simulated saline water by flowing the saline water through each of the cell units. The saline water was maintained at a temperature of about 77° F.

3. Once saturated the closure pressure on the cell units was increased to 1000 psi, at a rate of 100 psi per minute. The proppant was allowed to equilibrate for 30 minutes. All transducers and thermocouples were calibrated during this equilibrium period.

4. The flow rate, differential pressure and average width of the proppant pack were measured at 1000 psi in order to calculate conductivity and permeability. Five measurements were taken and averaged to arrive at each valve.

5. The cells were then shut in and the temperature was increased to the test temperature and allowed to equilibrate. The shut in period was from about 6 to 10 hours.

6. The pressure was then increased in 1000 or 2000 psi increments at 100 psi per minute, and the above measuring technique repeated. The proppant was allowed to equilibrate for 90 minutes for sand and 30 minutes for ceramics at each pressure.

7. The flow rates were set at 2.0 ml per minute and the conductivity and permeability were monitored continuously at the test temperature and closure pressures for 300 hours.

EQUIPMENT AND PROCEDURES-CASE II

The cell assembly described in Case I, was employed. The shims employed in each of the cell units, such as the shims 34, 36 of the cell unit 14, were fabricated of ⅜ inch slabs of Ohio Sandstone which were machined to fit the configuration of the passageway 40 of the cell body member 30. The shims 34, 36 were held in place by high temperatures silicone sealant which was applied to the edge of each of the shims 34, 36. The shims 34, 36 were held apart by a ⅛ inch spacer while the sealant was curing and during cell set up. The lower and upper pistons 32 and 38 were sealed in place with ethylene-propylene square rings. During the fracturing fluid flow/leakoff period both the lower and upper pistons 32, 38 were stabilized with set screws, such as set screws 76, 78. The slats were positioned within the recessed portions of each of the cell units, such as the slat members 124 and 126 positioned within the slots 120, 122, respectively, of the cell unit 14. Aluminum spacers (not shown) were positioned so as to extend between the slat and cell body member disposed therebelow so that application of hydraulic pressure could be imparted to the cell units without collapsing the proppant pack cavity 50. A pressure of 3000 psi was applied to the cell assembly 10, and thus to each of the cell units, by a press while the fracturing fluid was pressurized to 1000 psi.

The fracturing fluid was prepared and conditioned as hereinbefore described so as to simulate the conditions of the fracturing fluid entering the subterranean formation at a position approximately 50 feet from the well bore and at a depth of 5000 to 10000 feet. The conditioned fracturing fluid was passed through the cell unit, such as cell unit 14, at a shear rate of 40 to 50 reciprocal seconds. The conditioned fracturing fluid was flowed between the shims 34, 36 which had been previously saturated with the saline solution (i.e. a 2 percent KCl solution). The leakoff rate through each shims 34, 36 was monitored versus time. Upon the fluid exiting the cell units, such as cell unit 14, the fluid was directed to the high pressure knock-out vessels 212 and 214 where the sandladen fluid was collected and dumped while maintaining a constant pressure of 1000 psi on the system.

Generally, a complexed gel pump time of 240 minutes was performed on each test. The final slurry concentration varied for each proppant being tested. The amount of proppant was selected to obtain about 2 lbs. per square foot in the ⅛ inch slot between the shims 34, 36. The final slurry was flowed slowly into the cell and the cell shut in. The inlet conduit 154 having the distribution channel 160 formed therein was removed and replaced with the inlet conduit having a ⅛ inch hole therethrough, and a filter screen was disposed therein to confine proppant in the cell during closure. The set screws stabilizing the upper piston and the aluminum spacers were removed and a closure pressure of 1000 psi was applied to the cell assembly 10 while monitoring leakoff through the shims 34, 36. Once leakoff was completed at 1000 psi the cell assembly 10 was heated to the test temperature and the closure pressure increased to predetermined values representative of downhole conditions on which information and data were desired.

From the above description, it is apparent that the numerous data can be obtained from the cell assembly 10 of the present invention and because of the unique design of each of the cell units of the cell assembly 10, such as cell unit 14, the conditioning of the fracturing fluid, and the use of the core samples as shims 34, 36, that the data obtained simulates downhole conditions in a subterranean formation which have not heretofore been obtainable. Thus, the cell assembly 10, as well as the method for conditioning the fracturing fluid, constitute an advancement in the art in determining the conductivity and permeability of a fracture fluid system on proppants disposed in subterranean formations wherein such data simulates the actual downhole conditions.

It is clear that the present invention is well adapted to carry out the objects and to attain the ends and advantages mentioned herein as well as those inherent in the invention. While presently preferred embodiments of the invention have been described for purposes of this disclosure, numerous changes may be made which will readily suggest themselves to those skilled in art and which are accomplished within the spirit of the invention disclosed and as defined in the appended claims.

What is claimed is:

1. A cell assembly for determining the effects of gelled fracturing fluids on conductivity and permeability of proppants comprising:

a cell body member having an elongated passageway extending therethrough and a fluid inlet port formed in one end thereof and a fluid outlet port formed in an opposed end thereof, the inlet and outlet ports communicating with the passageway;

a lower piston member having a cross-sectional configuration substantially corresponding to the shape of the passageway of the cell body member, the lower piston member further characterized as having an upper portion, a lower portion, a set of ports extensive through a sidewall portion and an adjacent upper side thereof, and a groove formed about the peripheral edge of its upper portion, the lower piston member connected to the cell body member such that the upper portion thereof extends a selected distance into a lower portion of the passageway, the lower portion of the lower piston member extending outwardly from the cell body member;

first shim means disposed within the passageway of the cell body member adjacent the upper portion of the lower piston member for forming a fluid-tight seal with the cell body member, the first shim means comprising a substantially oval-shaped first shim member formed of quarried rock substantially corresponding to the structure of the subterranean formation, the first shim member having substantially planar, parallel upper and lower surfaces and being fabricated of a predetermined thickness;

second shim means disposed within the passageway of the cell body member for forming a fluid-tight seal with the cell body member, the second shim means disposed in a substantially parallel, spatial relationship with the first shim member so that a proppant pack cavity is formed therebetween and the inlet and outlet ports of the cell body member communicate with the proppant pack cavity, the second shim means comprising a substantially oval-shaped second shim member formed of quarried rock substantially corresponding to the structure of the subterranean formation, the second shim member having substantially planar, parallel upper and lower surfaces and being fabricated of a predetermined thickness;

gasket means disposed about a peripheral edge of each of the oval-shaped first and second shim members for cooperating with adjacently disposed portions of the cell body member defining the passageway such that a fluid-tight seal is formed therebetween and thereby preventing fluid flow between the oval shaped first and second shim members and the cell body member;

an upper piston member having a cross-sectional configuration substantially corresponding to the shape of the passageway of the cell body member, the upper piston member further characterized as having an upper portion, an opposed lower portion, a set of ports extensive through a sidewall portion and an adjacent lower side thereof, and a groove formed about the peripheral edge of its lower portion, the lower portion of the upper piston member positionable in the upper portion of the passageway in an abutting relationship with the oval-shaped second shim member such that the upper portion of the upper piston member extends outwardly from the cell body member, the upper piston member vertically movable within the passageway of the cell body member in response to force imparted thereto;

ring means positionable within the grooves formed in the upper and lower piston members for engaging the oval-shaped first and second shim members and the portion of the cell body member defining the passageway to form a fluid-tight seal therebetween;

manifold means for connecting the ports of the upper piston member and for connecting the ports of the lower piston member so that the rate of leak off of fluid through the oval-shaped first and second shim members can be determined; and means for injecting an effective amount of proppant into the proppant pack cavity via the fluid inlet port to provide from about 0.5 to about 4 pounds of proppant per square foot of the proppant pack cavity, and thereafter inject a fracturing fluid into the proppant pack cavity containing the proppant pack, the means for injecting the proppant and the fracturing fluid comprising:

an inlet conduit having a hollow injection member supported on one end thereof, the hollow injection member having a distribution channel formed therethrough shaped to substantially disperse fracturing fluids across an input surface of the proppant pack, a portion of the inlet conduit being disposed within the fluid inlet port of the cell body member such that a distal end of the hollow injection member is disposed substantially flush with the portion of the cell body member defining the adjacent end portion of the proppant pack passageway; and connector means for connecting the inlet conduit to the cell body member to form a fluid-tight seal therebetween.

2. The cell assembly of claim 1 wherein the upper and lower sides of the upper and lower piston members are provided with a plurality of grooves intersecting the ports extensive therethrough for directing fluid into the ports, and wherein the cell assembly further comprises:

heating means connected to the cell body member for heating the proppant pack disposed within the proppant pack cavity to a predetermined temperature.

3. The cell assembly of claim 2 further comprises:

insulating means for insulating the cell assembly such that the temperature of the proppant pack disposed within the proppant pack cavity may be controlled at a predetermined temperature.

4. A cell assembly for determining the effects of gelled fracturing fluids on conductivity and permeability of proppants comprising:

a cell body member having an elongated passageway extending therethrough and a fluid inlet port formed in one end thereof and a fluid outlet port formed in an opposed end thereof, the inlet and outlet ports communicating with the passageway;

a lower piston member having an upper portion, a lower portion and a groove formed about the peripheral edge of its upper portion, the lower piston member connected to the cell body member such that the upper portion thereof extends a selected distance into a lower portion of the passageway, the lower portion of the lower piston member extending outwardly from the cell body member;

first shim means disposed within the passageway of the cell body member adjacent the upper portion of the lower piston member for forming a fluid-tight seal with the cell body member, the first shim means comprising a substantially oval-shaped first shim member formed of quarried rock substantially corresponding to the structure of the subterranean formation, the first shim member having substantially planar, parallel upper and lower surfaces and being fabricated of a predetermined thickness;

second shim means disposed within the passageway of the cell body member for forming a fluid-tight seal with the cell body member, the second shim means disposed in a substantially parallel, spatial relationship with the first shim member so that a proppant pack cavity is formed therebetween and the inlet and outlet ports of the cell body member communicate with the proppant pack cavity, the second shim means comprising a substantially oval-shaped second shim member formed of quarried rock substantially corresponding to the structure of the subterranean formation, the second shim member having substantially planar, parallel upper and lower surfaces and being fabricated of a predetermined thickness;

gasket means disposed about a peripheral edge of each of the oval-shaped first and second shim members for cooperating with an adjacently disposed portion of the cell body member defining the passageway such that a fluid-tight seal is formed therebetween and thereby preventing fluid flow between oval shaped first and second shim members and the cell body member;

an upper piston member having an upper portion, an opposed lower portion, a set of ports extensive through a sidewall portion and an adjacent lower side thereof, and a groove formed about the peripheral edge of its lower portion, the lower portion of the upper piston member positionable in the upper portion of the passageway in an abutting relationship with the oval-shaped second shim member such that the upper portion of the upper piston member extends outwardly from the cell body member, the upper piston member vertically movable within the passageway of the cell body member in response to force imparted thereto;

ring means positionable within the grooves formed in the upper and lower piston members for engaging the oval-shaped first and second shim members and the portion of the cell body member defining the passageway to form a fluid-tight seal therebetween;

means for injecting an effective amount of proppant into the proppant pack cavity via the fluid inlet port to provide from about 0.5 to about 4 pounds of proppant per square foot of the proppant pack cavity, and thereafter inject a fracturing fluid into the proppant pack cavity containing the proppant pack, the means for injecting the proppant and the fracturing fluid comprising: an inlet conduit having a hollow injection member supported on one end thereof, the hollow injection member having a distribution channel formed therethrough shaped to substantially disperse fracturing fluids across an input surface of the proppant pack, a portion of the inlet conduit being disposed within the fluid inlet port of the cell body member such that a distal end of the hollow injection member is disposed substantially flush with the portion of the cell body member defining the adjacent end portion of the proppant pack passageway; and connector means for connecting the inlet conduit to the cell body member to form a fluid-tight seal therebetween; and wherein a plurality of cell body members are vertically stacked such that the passageway of each cell body member is aligned with the passageway of an adjacently disposed cell body member and each cell body member below the uppermost cell body member is engaged by the lower portion of the lower piston member thereabove, such lower portion member being positionable in the upper portion of the passageway of the cell body member disposed below in an abutting relationship with the oval-shaped second shim member disposed therein, the upper piston member extensive from the uppermost cell body member and the lower piston member connected to the lowermost cell body member such that a compressive force can be exerted on the upper and lower piston members of the uppermost and lowermost cell body members to impart compressive force throughout the proppant disposed in the proppant pack cavity of the cell assemblies, and wherein each cell body member is characterized as having a first and second side and each cell body member is provided with a plurality of ports extending through a sidewall of the cell body member which communicates with the proppant pack cavity, one of the ports being positioned substantially intermediate the first and second ends of the cell body member for monitoring pressure on a proppant pack disposed within the proppant pack cavity, a second port being positioned in close proximity to one end of the passageway and a third port being positioned within close proximity to the other end of the passageway, the second and third ports cooperating to permit the pressure drop ( ) of fluids passing through the proppant pack to be determined.

* * * * *

UNITED STATES PATENT AND TRADEMARK OFFICE
CERTIFICATE OF CORRECTION

PATENT NO. : 4,922,758

DATED : May 8, 1990

INVENTOR(S) : Glenn S. Penny

It is certified that error appears in the above-identified patent and that said Letters Patent is hereby corrected as shown below:

Column 3, line 15, delete "Mode" and substitute
--Model-- therefor;

Column 3, line 55, delete "sepcific" and substitute
--specific-- therefor;

Column 3, line 61, delete "reprsentative" and substitute
--representative-- therefor;

Column 4, line 15, delete "indicatead" and substitute
--indicated-- therefor;

Column 4, line 49, delete "tansferred" and substitute
--transferred-- therefor;

Column 4, line 66, delete "positoin" and substitute
--position-- therefor;

Column 5, line 29, delete "respsectively," and substitute
--respectively,-- therefor;

Column 7, line 34, delete "loer" and substitute --lower--
therefor;

Column 11, lines 52-53, delete "trasnducer" and substitute
--transducer-- therefor; and

UNITED STATES PATENT AND TRADEMARK OFFICE
CERTIFICATE OF CORRECTION

PATENT NO. : 4,922,758

DATED : May 8, 1990

INVENTOR(S) : Glenn S. Penny

It is certified that error appears in the above-identified patent and that said Letters Patent is hereby corrected as shown below:

Column 12, line 33, delete "5/8 inch" and substitute
--3/8 inch-- therefor.

Signed and Sealed this

Seventh Day of April, 1992

Attest:

HARRY F. MANBECK, JR.

*Attesting Officer*      *Commissioner of Patents and Trademarks*